US00PP14884P2

(12) United States Plant Patent
Pieters

(10) Patent No.: US PP14,884 P2
(45) Date of Patent: Jun. 8, 2004

(54) CHRYSANTHEMUM PLANT NAMED 'LAIKA'

(50) Latin Name: *Chrysanthemum ajania pacificum*
Varietal Denomination: Laika

(75) Inventor: Luc Remi Johan Pieters, Staden-Oostnieuwkerke (BE)

(73) Assignee: Pieters, Joseph & Luc B.V.BA, Staden-Oostnieuwkerke (BE)

( * ) Notice: Subject to any disclaimer, the term of this patent is extended or adjusted under 35 U.S.C. 154(b) by 0 days.

(21) Appl. No.: 10/654,480

(22) Filed: Sep. 2, 2003

(51) Int. Cl.[7] ..... A01H 5/00
(52) U.S. Cl. ..... Plt./284
(58) Field of Search ..... Plt./284

*Primary Examiner*—Anne Marie Grunberg
(74) *Attorney, Agent, or Firm*—C. A. Whealy

(57) ABSTRACT

A new and distinct cultivar of Chrysanthemum plant named 'Laika', characterized by its numerous small inflorescences without ray florets; freely branching growth habit; early flowering response; and good postproduction longevity.

1 Drawing Sheet

Botanical classification/cultivar designation: *Chrysanthemum ajania pacificum* cultivar Laika.

BACKGROUND OF THE INVENTION

The present invention relates to a new and distinct cultivar of Chrysanthemum plant, botanically known as *Chrysanthemum ajania pacificum* and referred to by the name 'Laika'.

The new Chrysanthemum is the product of a planned breeding program conducted by the Inventor in Staden-Oostnieuwkerke, Belgium. The objective of the breeding program is to develop new cultivars of *Chrysanthemum ajania pacificum* with unique inflorescence forms, attractive ray and disc coloration and little to no pollen.

The new Chrysanthemum originated from a open-pollination made by the Inventor in October, 2000, in Staden-Oostnieuwkerke, Belgium, of the *Chrysanthemum ajania pacificum* cultivar Zarros Rose, not patented, as the female, or seed, parent with an unknown Chrysanthemum selection, not patented, as the male, or pollen, parent. The new Chrysanthemum was discovered and selected by the Inventor as a single plant within the progeny of the stated open-pollination in a controlled environment in Staden-Oostnieuwkerke, Belgium.

Asexual reproduction of the new Chrysanthemum by terminal cuttings in Staden-Oostnieuwkerke, Belgium has shown that the unique features of this new Chrysanthemum are stable and reproduced true to type in successive generations.

BRIEF SUMMARY OF THE INVENTION

The cultivar Laika has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Laika'. These characteristics in combination distinguish 'Laika' as a new and distinct cultivar:

1. Numerous small inflorescences without ray florets; typically grown as a spray type.
2. Freely branching growth habit.
3. Early flowering response.
4. Good postproduction longevity.

Plants of the new Chrysanthemum can be compared to plants of the female parent, the cultivar Zarros Rose. In side-by-side comparisons conducted in Staden-Oostnieuwkerke, Belgium, plants of the new Chrysanthemum differed from plants of the cultivar Zarros Rose in the following characteristics:

1. Natural flowering date for plants of the new Chrysanthemum was about four to five weeks later than natural flowering date for plants of the cultivar Zarros Rose.
2. Plants of the new Chrysanthemum had yellow-colored inflorescences whereas plants of the cultivar Zarros Rose had pink-colored inflorescences.

Plants of the new Chrysanthemum can also be compared to plants of the cultivar Silver and Gold, not patented. In side-by-side comparisons conducted in Staden-Oostnieuwkerke, Belgium, plants of the new Chrysanthemum differed from plants of the cultivar Silver and Gold in the following characteristics:

1. Plants of the new Chrysanthemum were more rounded than plants of the cultivar Silver and Gold.
2. Plants of the new Chrysanthemum and plants of the cultivar Silver and Gold differed in leaf coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph at the top of the sheet comprises a side perspective view of a typical flowering plant of 'Laika'.

The photograph at the bottom of the sheet comprises a close-up view of the lower and upper surfaces of typical leaves (top) and typical inflorescences (bottom) of 'Laika'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the spring in Staden-Oostnieuwkerke, Belgium, under commercial practice in a glass-covered greenhouse. Plants were initially given long day/short night treatments followed by short day/long night treatments to induce flower initiation and development. During the production of the plants, day temperatures were about 15° C. and night temperatures were about 13° C. Plants were about four months from planting into 13-cm containers when the photographs and the description were taken.

Botanical classification: *Chrysanthemum ajania pacificum* cultivar Laika.

Commercial classification: Chrysanthemum without ray florets typically grown as a spray-type potted plant.

Parentage:

*Female or seed parent.*—*Chrysanthemum ajania pacificum* cultivar Zarros Rose, not patented.

*Male or pollen parent.*—Unknown selection of *Chrysanthemum ajania pacificum,* not patented.

Propagation:

*Type.*—Terminal tip cuttings.

*Time to initiate roots, summer.*—About 10 days at 25° C.

*Time to initiate roots, winter.*—About 12 days at 20° C.

*Time to produce a rooted cutting, summer.*—About 14 days at 25° C.

*Time to produce a rooted cutting, winter.*—About 21 days at 20° C.

*Root description.*—Fine, fibrous, and freely branching; white in color.

Plant description:

*Appearance.*—Herbaceous potted Chrysanthemum typically grown as a spray type. Stems upright and outwardly spreading; plants with rounded crown. Freely branching with lateral branches potentially developing at every node; pinching is not required; dense and full plants.

*Plant height.*—About 22 cm.

*Plant width.*—About 26 cm.

*Lateral branches.*—Length: About 7 to 12 cm. Diameter: About 2 mm. Strength: Strong, flexible. Texture: Pubescent. Color: 146D.

*Foliage description.*—Arrangement: Alternate. Length: About 2 to 5 cm. Width: About 1.5 to 5.5 cm. Apex: Acute. Base: Attenuate. Margin: Palmately lobed. Texture: Upper and lower surfaces pubescent; veins prominent on lower surface. Color: Developing foliage, upper surface: 137A. Developing foliage, lower surface: 191A. Fully expanded foliage, upper surface: 147A. Fully expanded foliage, lower surface: 191A. Venation, upper surface: 146B. Venation, lower surface: 191B. Petiole length: About 0.5 to 1.5 cm. Petiole diameter: About 1 mm. Petiole color: 137C.

Inflorescence description:

*Appearance.*—Inflorescences without ray florets. Inflorescences borne on terminals above foliage. Disk florets develop acropetally on a capitulum. Slightly fragrant. Typically grown as a spray-type.

*Flowering response.*—Under natural conditions, plants flower in September in the Northern Hemisphere. At other times of the year, inflorescence initiation and development can be induced under short day/long night conditions (at least 13.5 hours of darkness). Early flowering; plants exposed to long day/short night conditions followed by photoinductive short day/long night conditions flower about 53 days later.

*Postproduction longevity.*—Inflorescences maintain good color and substance for about four weeks in an interior environment.

*Quantity of inflorescences.*—Freely flowering, about five to six inflorescences develop per lateral stem.

*Inflorescence bud.*—Height: About 4 mm. Diameter: About 5 mm. Shape: Ovoid. Color: 144A to 144B.

*Inflorescence size.*—Diameter: About 9 mm. Depth (height): About 6 mm.

*Ray florets.*—None observed.

*Disc florets.*—Arrangement: Massed at center of receptacle. Shape: Tubular. Apex: Five-pointed. Length: About 5 mm. Width: About 0.7 mm. Number of disc florets per inflorescence: About 100. Color: Immature: 145C to 145B. Mature: Close to 12A.

*Peduncles.*—Length: About 1 to 2 cm. Diameter: About 1 mm. Angle: About 35° from vertical. Strength: Wiry, flexible. Texture: Smooth; glabrous. Color: 146D.

*Reproductive organs.*—Androecium: Present on disc florets. Anther color: 7A. Pollen color: 15A. Gynoecium: Present on disc florets.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Laika', as illustrated and described.

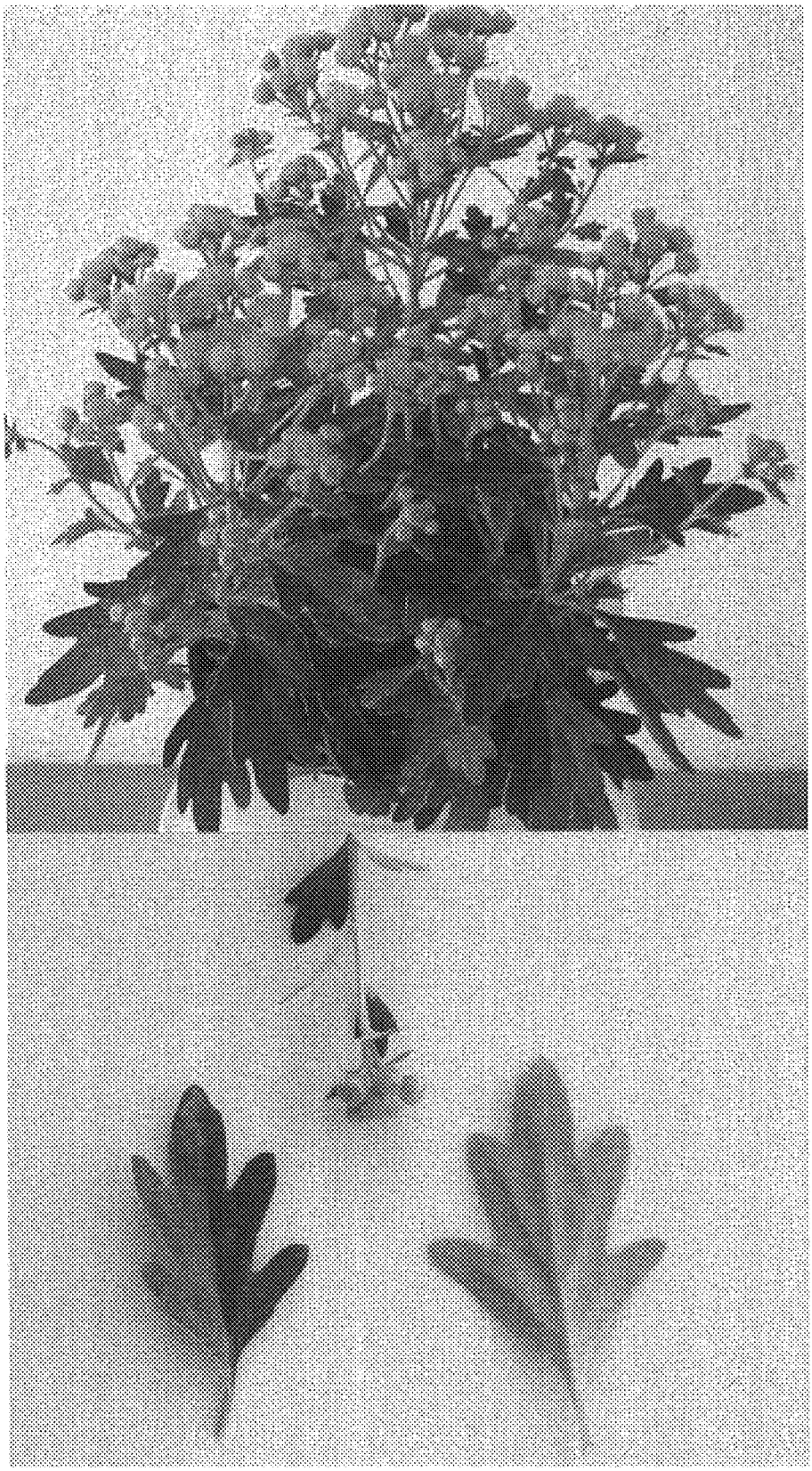

* * * * *